United States Patent [19]

Häberle et al.

[11] 4,393,220
[45] Jul. 12, 1983

[54] 2-ALKENYL AND 2-ALKYNYL SUCCINIC ACID N-(3,5-DICHLOROPHENYL)IMIDES

[75] Inventors: Norman Häberle, Munich; Otto Eberle, Ottobrunn; Walter Hafner, Furth, all of Fed. Rep. of Germany

[73] Assignee: Consortium für elektrochemische Industrie GmbH, Munich, Fed. Rep. of Germany

[21] Appl. No.: 249,323

[22] Filed: Mar. 31, 1981

[30] Foreign Application Priority Data

Apr. 9, 1980 [DE] Fed. Rep. of Germany ....... 3013566

[51] Int. Cl.³ .................... A01N 37/32; C07D 207/40
[52] U.S. Cl. .................................. 548/545; 424/274; 71/95
[58] Field of Search .............. 260/326.5 FM; 548/545

[56] References Cited

U.S. PATENT DOCUMENTS 3,538,114 11/1970 Himmele et al. ................... 548/545

FOREIGN PATENT DOCUMENTS 2740848 9/1977 Fed. Rep. of Germany ...... 548/544
52-12161 1/1977 Japan ................................. 548/547

Primary Examiner—Donald G. Daus
Assistant Examiner—D. B. Springer
Attorney, Agent, or Firm—Allison C. Collard; Thomas M. Galgano

[57] ABSTRACT

The invention relates to fungicidally active compositions that contain at least one compound of the general formula

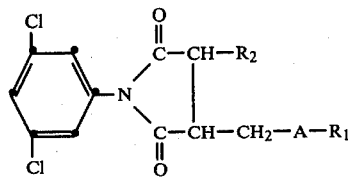

and/or a compound of the formula

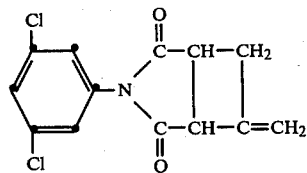

in which:
A denotes the —CH=CH— or —C≡C— group and $R_1$ and $R_2$ represent hydrogen or methyl.

The active substances according to the invention can be obtained by reacting correspondingly substituted succinic acids, or acid halides, anhydrides or esters thereof, with 3,5-dichloroaniline.

2 Claims, No Drawings

2-ALKENYL AND 2-ALKYNYL SUCCINIC ACID N-(3,5-DICHLOROPHENYL)IMIDES

The invention relates to the manufacture of N-phenylsuccinic acid imides and their use as fungicides.

N-(3,5-dichlorophenyl)-succinimide compounds having fungicidal properties are already known. A comprehensive discussion in that respect is given in R. Wegler, *Chemie der Pflanzenschutz- und Schadlingsbekampfungsmittel,* volume 4, page 201 ff., Springer-Verlag, 1977.

European Patent Application No. 000 1395 similarly describes fungicidal N-(3,5-dichlorophenyl)-succinimides that carry, on the succinic acid skeleton, especially cycloaliphatic substituents, but also, for example, isobutenyl radicals or branched alkyl groups.

German Offenlegungsschrift No. 19 40 032 also mentions fungicidal N-(3,5-dichlorophenyl)-succinimides that have aromatic substituents or smaller saturated aliphatic substituents on the succinic acid radical.

Furthermore, a number of highly substituted N-(3,5-dichlorophenyl)-succinimides have been disclosed as microbicides in German Offenlegungsscrift No. 20 12 656, especially those having hetero atoms in the substitution moiety.

German Offenlegungsschrift No. 15 42 835 describes compounds of this kind also as herbicides.

It is therefore known according to the state of the art that succinic acid imides of 3,5-dichloroaniline possess properties that are fungitoxic to a greater or lesser extent.

The aim of the invention was to find compounds from among this class that, according to the following criteria, have special advantages:
(1) Ready availability with regard to the chemical method of synthesis;
(2) High fungitoxicity, i.e., high effectiveness in very small doses;
(3) Broad range of action;
(4) Well tolerated by higher plants; and
(5) Harmlessness towards higher forms of life.

It has been found that the criteria mentioned above are satisfied to a special degree by a small select group of compounds, the use of which, as fungicides, is the subject of the invention.

The invention therefore provides fungicidally active compositions that contain at least one compound of the general formula

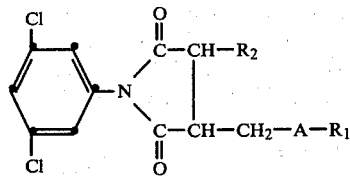

and/or a compound of the formula

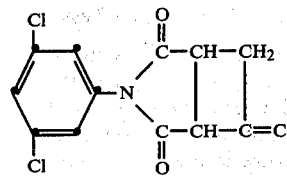

in which
A denotes the —CH=CH— or —C≡C— group;
$R_1$ represents H— or $CH_3$—; and
$R_2$ may be H— or $CH_3$—.

A characteristic of all the compounds to be used in accordance with the invention is that they carry straight-chain substituents having a multiple carbon bond that is not conjugated with the carbonyl function of the succinic acid radical. Surprisingly, compounds that have this feature in combination with substituents of specific chain length—namely, those having 3 to 4 chain members, exhibit especially favorable properties.

The fungicides according to the invention are suitable, without their field of use being limited thereto, for example, for use in viniculture, in strawberry cultivation, in horticulture, especially in salad crops, in rape cultivation or in ornamental plants (cyclamens, geraniums, etc.). Use as seed dressing was found to be a further application according to the invention.

The active substances according to the invention are successful in controlling fungal diseases. They have been found, for example, to be highly effective against *Botrytis cinerea* (grey mold). Further examples of fungi such as *Alternaria solani, Fusarium nivale, Septoria nodorum, Verticillium dahliae, Penicillium glaucum,* types of Sclerotinia (for example, Sclerotinia Sclerotiorum), Phomalingam and others. Furthermore, the active substances according to the invention can be used successfully against phytopathogenic fungi that adhere to the seeds, such as, for example, *Tilletia tritici* (wheat bunt). The need for such new fungicides is evident not only from their outstanding effectiveness, but also from the property of many types of fungus to produce strains that are resistant to the fungicides already in use.

A special advantage of the active substances to be used according to the invention is, moreover, their physiological harmlessness towards higher forms of life. Since fungicides are frequently used in the case of foodstuffs, it is precisely that property that is of great value for modern agriculture.

The succinic acid imides according to the invention can be manufactured in a manner known per se. The process is characterized in that the correspondingly substituted succinic acid, or an acid halide, acid anhydride or acid ester thereof, is reacted, optionally in the presence of a tertiary organic base such as, for example, pyridine or triethylamine, with 3,5-dichloroaniline.

In certain cases, it may be advantageous to use, for the reaction, water-binding or acid-binding agents such as, for example, alkali metal or alkaline earth metal carbonates, hydroxides or oxides, especially soda, potash, magnesia, or burnt, slaked or aerated lime.

If the necessary substituted succinic acid derivatives are not commercially available, they can be manufactured according to known processes. The processes are characterized in that corresponding olefins or acetylenes are reacted with maleic acid anhydride, optionally in suitable pressure vessels. Methylenecyclobutanesuccinic acid is prepared in a similar manner by using allene.

The active substances according to the invention can be applied on their own or in admixture with other suitable plant-protecting agents. In general, however, they are used as mixtures with solid or liquid diluents, or as solutions in solid or liquid solvents, containing from 0.01 to 95% by weight of active substances.

The mixtures or solutions are generally prepared in the form of emulsion concentrates, pastes, sprayable powders, granules or micro-capsules.

Emulsion concentrates and pastes generally contain from 10 to 60% by weight, preferably from 15 to 40% by weight, of active substances, from 2 to 25% by weight of dispersants, and organic solvents and/or water.

Sprayable powders usually contain from 10 to 80% by weight, preferably from 15 to 70% by weight, of active substance, from 1 to 10% by weight of dispersants, and from 10 to 89% by weight of inert substances.

Granules and dusting preparations contain, in addition to inert substances, binders and/or coating substances, from 1 to 10% by weight, preferably from 5 to 10% by weight, of active substance. The following are used according to the invention:

as dispersants, e.g.:
  alkylsulphonates and arylsulphonates, methylcellulose, polymeric sulphonic acids and salts thereof, polyalcohols, fatty acid esters, fatty alcohol ethers, and fatty amines;
as organic solvents, e.g.:
  alcohols, such as ethanol and butanol, dimethylformamide, dimethyl sulphoxide, N-methylpyrrolidone, and aromatic compounds, such as toluene and xylene;
as inert substances, e.g.:
  kaolin, China clay, talc, calcium carbonate, highly dispersed silica, silica gels, kieselguhr, diatomaceous earth, pumice, crushed maize, and thickening agents, such as starch and carboxymethylcellulose; and
as binders, e.g.:
  magnesium sulphate, gypsum, and gum arabic.

The composition of the fungicides according to the invention is, for example, as follows:

(1) Emulsion concentrate:
  20% by weight of active substance;
  10% by weight of commercial ethoxylated anhydrosorbitol monolaurate (trademark "Tween Twenty"); and
  70% by weight of dimethylformamide.

(2) Sprayable powder:
  20% by weight of active substance;
  5% by weight of ammonium lignin sulphonate (trademark "Totanin")'
  10% by weight of sodium oleylmethyl tauride (trademark "Arkopon T Konz"); and
  65% by weight of kaolin.

The application quantities of the active substances may vary within wide ranges. In the case of seed treatment, quantities of active substances of from 0.05 to 25 g/kg of seed are generally required.

The active substances according to the invention may be applied in any suitable form. The following are mentioned by way of example: pouring, syringing, spraying, scattering, coating and treatment of the seed (dressing).

The methods of preparing the compounds to be used according to the invention, and their fungicidal effectiveness, are illustrated below with reference to the following examples:

EXAMPLE 1

Preparation of 2-allylsuccinic acid N-(3,5-dichlorophenyl)-imide 28 g (0.2 moles) of allylsuccinic acid anhydride, 32.4 g (0.2 moles) of 3,5-dichloroaniline, 0.6 g of triethylamine and 150 ml of xylene are reacted at 125° C., with stirring. The water produced during the reaction is removed azeotropically by way of a water separator. The duration of the reaction is 4 hours. The solvent is subsequently drawn off and the residue is recrystallized from ethyl acetate with the addition of active carbon. The product has a melting point of 121° C. The yield is 89.4% of the theoretical yield.

EXAMPLE 2

Preparation of 2-allyl-3-methylsuccinic acid N-(3,5-dichlorophenyl)-imide 90.5 g (0.5 moles) of 2-allylmalonic acid diethyl ester are reacted in diethylene glycol dimethyl ether with 0.5 moles of alcohol-free sodium ethoxide. 0.5 moles of 2-bromopropionic acid ethyl ester is added dropwise to this solution, with stirring. The mixture is heated for a further 2 hours under reflux and the solvent is then removed. The residue is subsequently subjected to hydrolysis in alcoholic KOH. After drying the organic layer that has separated, it is fractionated. The desired 2-allyl-1-methylethane-tricarboxylic acid 1,2,2-triethyl ester boils under 0.02 torr at 92° to 95° C. The ester is hydrolyzed in alcoholic KOH and, after working up in the customary manner, is decarboxylated at 170° C. with water being split off. The anhydride of 2-allyl-3-methylsuccinic acid (b.p. at 0.1 torr: 108° to 110° C.) is obtained in a 96% yield (based on the ester).

The anhydride is reacted with 3,5-dichloroaniline as described in Example 1.

The desired product has a melting point of 131° C.

EXAMPLE 3

3-Methylenecyclobutane-1,2-dicarboxylic acid N-(3,5-dichlorophenyl)-imide.

In a steel autoclave of 2 liters capacity, equipped with a stirrer, 500 g (5.1 moles) of maleic acid anhydride, 645 ml of benzene and 0.25 g of hydroquinone are cooled to −70° C., with stirring. After evacuation to 20 torr, 100 g (2.5 moles) of allene are drawn into the autoclave by suction. The reaction mixture is then heated to 200° C., with stirring. After 8 hours, the reaction mixture is cooled to 25° C., relieved of pressure, and unreacted allene is collected in a cold trap. The benzene solution is decanted off and the residue is dissolved in 500 ml of acetone. The combined benzene and acetone solutions are subsequently worked up by distillation. After removing the solvents, up to 250 g of maleic acid anhydride are recovered at between 110° and 115° C. under a pressure of 40 torr. Finally, 119 g of the crude product of the desired anhydride are obtained under 3 torr in a fraction boiling at 70° to 125° C. The crude product is subsequently rectified under 25 torr at 155° to 159° C. The yield is 25%.

The anhydride is reacted with 3,5-dichloroaniline as described in Example 1. The resulting product has a melting point of 119° C.

EXAMPLE 4

Grape Juice Test 20 ml of a nutrient solution consisting of grape juice and distilled water in a weight ratio of 1:1 are poured into glass petri dishes and the active substances listed in Table 1 are added thereto in the stated concentrations. Each test mixture is then inoculated with 50 µl of a suspension of Botrytis spores, prepared by washing the Botrytis spores from an agar culture with distilled water.

After incubation periods of 10 to 20 days, respectively, at 20° C., the extent of fungal development on the surface of the nutrient solution is assessed.

The effectiveness is calculated, as a percentage, according to the following equation:

$$100 - \frac{\text{fungal growth, treated}}{\text{fungal growth, untreated}} \times 100$$

TABLE 1

Effectiveness against *Botrytis cinerea* in grape juice test at active substance concentration of 10 ppm

| active substance | % effectiveness after 10 days | % effectiveness after 20 days |
|---|---|---|
| 2-allylsuccinic acid N—(3,5-dichlorophenyl)-imide | 100 | 100 |
| 2-(but-2-en-1-yl)-succinic acid N—(3,5-dichlorophenyl)-imide | 100 | 100 |
| 2-propargylsuccinic acid N—(3,5-dichlorophenyl)-imide | 100 | 100 |
| 3-methylenecyclobutane-1,2-dicarboxylic acid N—(3,5-dichlorophenyl)-imide | 100 | 100 |

Comparison Example 1

The test set-up and procedure are the same as those described in Example 4. In contrast, however, the concentration of the active substance is 10 times as high, i.e., 100 ppm.

TABLE 2

Effectiveness against *Botrytis cinerea* in grape juice test at active substance concentration of 100 ppm

| active substance | % effectiveness after 10 days | % effectiveness after 20 days |
|---|---|---|
| 2-allylsuccinic acid N—(3,4-dichlorophenyl)-imide | 0 | 0 |

EXAMPLE 5

Spore Germination Test

50 μl of a solution or suspension containing 500 ppm of the active substance are introduced into the hollow of hollow-ground slides together with 50 μl of a spore suspension prepared by washing the spores from an agar culture with a nutrient solution containing, per liter, 10 g of sugar, 1 g of glycol, 1 g of $KH_2PO_4$ and 0.5 g of $MgSO_4$.

The slides are kept at 20° C. for 48 hours in a petri dish, the base of which is covered with a moistened filter paper.

The ratio of germinated and ungerminated spores is then compared with an untreated control sample.

The effectiveness is calculated, as a percentage, according to the following equation:

$$100 - \frac{\text{number of germinated spores, treated}}{\text{number of germinated spores, untreated}} \times 100$$

The results are shown in Table 3.

Comparison Example 2

The test set-up and procedure are the same as those described in Example 5.

The results are shown in Table 4.

TABLE 3

Fungitoxicity towards fungus spores at an active substance concentration of 500 ppm

| active substance | Alternaria solani | Botrytis cinerea | Fusarium nivale | Penicillium glaucum | Septoria nodorum |
|---|---|---|---|---|---|
| 2-allylsuccinic acid N—(3,5-dichlorophenyl)-imide | 80 | 100 | 60 | 80 | 60 |
| 2-(but-2-en-1-yl)-succinic acid N—(3,5-dichlorophenyl)-imide | 70 | 80 | 80 | 80 | 60 |
| 2-propargylsuccinic acid N—(3,5-dichlorophenyl)-imide | 80 | 100 | 80 | 80 | 40 |
| 3-methylenecyclobutane-1,2-dicarboxylic acid N—(3,5-dichlorophenyl)-imide | 80 | 100 | 100 | 80 | 60 |

TABLE 4

Fungitoxicity of comparison active substances towards fungus spores at an active substance concentration of 500 ppm

| active substance | Alternaria solani | Botrytis cinerea | Fusarium nivale | Penicillium glaucum | Septoria nodorum |
|---|---|---|---|---|---|
| 2-allylsuccinic acid N—(3,4-dichlorophenyl)-imide | 0 | 0 | 0 | 0 | 0 |
| 2-cyclohexenesuccinic acid N—(3,5-dichlorophenyl)-imide | 30 | 25 | 0 | 0 | 30 |
| 3-(3,5-dichlorophenyl)-1-isopropylcarbamoyl-hydantoin Trademark Rovral | 0 | 100 | 0 | 60 | 30 |
| vinchlozolin Trademark Ronilan | 30 | 100 | 40 | 30 | 40 |

In particular, comparison of the fungitoxic data of 2-allylsuccinic acid N-(3,5-dichlorophenyl)-imide with those of the preparations for comparison from Comparison Example 1 and the first two succinic acid derivatives mentioned in Comparison Example 2 is informative.

The two comparison preparations differ from each other, in one case, by the type of chlorine substitution on the phenyl group (3,4 instead of 3,5) and, in the other case, by the substitution on the succinic acid radical. It is apparent that only a combination of the individual components of the molecule—succinic acid imide+N-(3,5-dichlorophenyl)+specific selection of the substituent on the succinic acid radical—results in the surprisingly highly fungitoxic properties.

Furthermore, the results of Example 5 and Comparison Example 2 demonstrate the broader range of action of the compounds according to the invention. This property is often of decisive importance; for example, attendant fungi, such as *Alternaria solani* and *Penicillium glaucum* often occur together with *Botrytis cinerea*. If a fungicide is directed at only one particular strain of fungus, increased growth of the types of attendant fungus will often be observed. Good prospects of success in the treatment of fungal disease can accordingly be ensured only if the fungicide used has such a broad range of action that it controls the entire complex of the fungal disease.

EXAMPLE 6

Seed Dressing Test

Healthy wheat seed grains are uniformly infected with spores of *Tilletia tritici*. The infected seed grains are subsequently dressed carefully with the active substances according to the invention, prepared in the form of dry dressings.

After being dressed, the wheat grains are placed in dishes of damp earth. Incubation is carried out at from 14° to 17° C. in a dark drying cupboard. After 48 hours, the spores adhering to the grains are removed by pressing the grains into loam/earth.

After incubation for a further 8 days at from 14° to 17° C. in the drying cupboard, the ratio of germinated and ungerminated spores as compared with an untreated control is determined under the microscope.

The action of the active substances according to the invention is given as percentage germination inhibition.

TABLE 5

Dressing test against wheat bunt (*Tilletia tritici*)

| active substance | Effectiveness % | |
|---|---|---|
| | at 1000 ppm active substance concentration | at 100 ppm active substance concentration |
| 2-allylsuccinic acid N—(3,5-dichlorophenyl)-imide | 100 | 85 |
| 2-(but-2-en-1-yl)-succinic acid N—(3,5-dichlorophenyl)-imide | 100 | 85 |

Thus, while only several examples of the present invention have been shown and described, it will be obvious that many changes and modifications may be made thereunto, without departing from the spirit and scope of the invention.

What is claimed is:

1. A compound of the formula

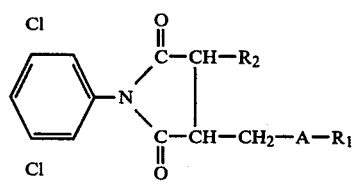

in which
A denotes the —CH=CH— or —C∇C— group and R₁ and R₂ represent hydrogen or methyl.

2. The compound 2-allylsuccinic acid N-(3,5-dichlorophenyl)-imide.

* * * * *